United States Patent
Usui

[11] Patent Number: 6,099,556
[45] Date of Patent: Aug. 8, 2000

[54] METHOD OF CONTROLLING EXOTHERMIC REACTION OF AN EXOTHERMIC COMPOSITION, THE EXOTHERMIC COMPOSITION, AN EXOTHERMIC DEVICE AND AN APPLICATION PAD

[75] Inventor: Akio Usui, Tochigi, Japan

[73] Assignee: Kabushiki Kaisha Genchi Kenkyusho, Tochigi, Japan

[21] Appl. No.: 08/645,858

[22] Filed: May 14, 1996

[30] Foreign Application Priority Data

May 27, 1995 [JP] Japan ................................. 7-152152

[51] Int. Cl.⁷ ........................................... A61F 7/00
[52] U.S. Cl. ................ 607/114; 126/263.01; 126/263.02
[58] Field of Search ..................... 607/108, 112, 607/114; 62/4; 126/236.01, 236.02, 236.1, 263.01, 263.02, 263.1

[56] References Cited

U.S. PATENT DOCUMENTS

| | | | |
|---|---|---|---|
| 4,366,804 | 1/1983 | Abe | 126/263.02 |
| 4,925,743 | 5/1990 | Ikeda et al. | 607/114 |
| 5,046,479 | 9/1991 | Usui | 126/263.02 |
| 5,233,981 | 8/1993 | Miyashita | 126/263.01 |
| 5,339,796 | 8/1994 | Manker | 126/263 |

FOREIGN PATENT DOCUMENTS 2255722  11/1992  United Kingdom ..................... 600/15

Primary Examiner—Jack W. Lavinder
Assistant Examiner—David M. Ruddy
Attorney, Agent, or Firm—Edwin E. Greigg; Ronald E. Greigg

[57] ABSTRACT

An exothermic composition, enclosed in a container at least part of which is gas-permeable, generates heat in the presence of air. The exothermic composition includes a water absorber having a water absorptive ability reversibly variable with temperature variations. The water absorber releases adsorbed water, at above a predetermined temperature, to increase free moisture around a metal powder, thereby retarding the exothermic reaction.

17 Claims, 6 Drawing Sheets

METHOD OF CONTROLLING EXOTHERMIC REACTION OF AN EXOTHERMIC COMPOSITION, THE EXOTHERMIC COMPOSITION, AN EXOTHERMIC DEVICE AND AN APPLICATION PAD

BACKGROUND OF THE INVENTION (1) Field of the Invention

The present invention relates to a method of controlling an exothermic reaction, using water, of an exothermic composition, the exothermic composition, an exothermic device and an application pad. More particularly, the invention relates to an exothermic reaction of an exothermic composition, the exothermic composition, an exothermic device and an application pad, in which the exothermic reaction is controlled so that an exothermic temperature is maintained below a predetermined temperature to enhance safety when applied to a living body such as a human body.

(2) Description of the Related Art

In recent years, hot compresses and body warmers have been employed which utilize, as a heat source, the heat of a reaction with oxygen in the air of an exothermic composition containing a metal powder, a metallic chloride and water as essential components thereof. One familiar example is a disposable body warmer in which an exothermic composition including a metal powder, a metallic chloride, water, a catalyst and an exothermic auxiliary is enclosed in a flat pouch gas-permeable in one or both surfaces thereof.

Some disposable body warmers have an adhesive layer formed on one surface thereof to be pasted directly or through underwear to the skin. Where this type of body warmer is used as a hot compress, the adhesive layer may include skin absorbable medication, a far infrared radiator and a magnetic substance dispersed therein.

Where this type of exothermic composition is used as a body warmer or hot compress, it is necessary to generate heat of a predetermined temperature, e.g. 37° C. or above, higher than the average body temperature in order to provide a sufficient heating or therapeutic effect. On the other hand, it is desirable to control the heat below 43° C. or so in order to prevent a low-temperature burn. This is because a low-temperature burn could be inflicted if a temperature exceeding 43° C. were maintained for a long time.

In an initial attempt to control the exothermic temperature of the exothermic composition, the gas permeability of the pouch was controlled to control the quantity of air (quantity of oxygen) taking part in the reaction. With this method, water vapor is produced inside the pouch in an increasing quantity with a temperature increase resulting from the exothermic reaction. The water vapor adheres to pores of the pouch to vary its permeability. It is therefore difficult to control the permeability in a steady manner.

That is, water vapor adheres in varied quantities to the pores of the pouch having the same permeability, depending on the type of the pouch, e.g. pouch materials, filling agents, or whether a surface activating treatment has been given or not. Thus, it has been impossible to obtain an exothermic device of reliable quality.

A method proposed subsequently of controlling the heat of the exothermic composition consisted in controlling the water-vapor permeability of the pouch. Compared with controlling the exothermic temperature of the exothermic composition by means of gas permeability, this method realizes a strict temperature control, to provide an exothermic device assuring increased safety.

In order to secure both heating or therapeutic effect and safety, a gas-permeable film used has a water-vapor permeability specified by the ASTM method (E-96-80D method), with a narrow range of variation at plus/minus 5 to 10% of the standard value, or plus/minus 20 to 35% of the standard value at most.

The flat pouch gas-permeable in one or both surfaces thereof has the one surface or both surfaces formed of a gas-permeable film. The gas-permeable film is formed by drawing a plastic film, or laminating a gas-permeable reinforcing base material such as a nonwoven fabric on the drawn plastic film.

However, in manufacturing an exothermic device, it has always been difficult to reduce the range of variation in the water-vapor permeability of a gas-permeable film as noted above. Where a material having a certain range of such variation is used, an increased number of defective gas-permeable film products are manufactured, resulting in high cost and a waste of resources.

Even when gas-permeable film products are limited to a particular range (what is known as a delivery specification) of water-vapor permeability, all of the products received are not necessarily in this range. Some of the gas-permeable products received are off-specification products. Consequently, some pouches are formed of the gas-permeable film with off-specification water-vapor permeability. The exothermic composition may have variations, and environment such as ambient temperature or humidity may be different also.

As a result, variations occur in the maximum exothermic temperature, and high temperatures exceeding a predetermined temperature cause varied harmful effects.

Specifically, in the case of an exothermic device or application pad applied to the human body, for example, varied harmful effects such as blisters, erythema or other conditions are caused through a low-temperature burn. In practice, therefore, instructions are given regarding use of the exothermic device or application pad, for example, in the form of specifying sites of application, forbidding repeated application to the same site, forbidding use of a belt or the like to press the exothermic device or application pad, or forbidding direct application to the skin. Various other instructions may be essential, such as instructions to stop use immediately when an excessive heat is felt or to avoid use during a period of sleep.

Depending on use environment for the exothermic device, particularly at a high ambient temperature, the exothermic reaction may progress at too high a rate, whereby the exothermic temperature exceeds an intended maximum exothermic temperature. This poses a disadvantage in safety enhancement.

Inventor has made intensive research in an attempt to realize an extended use period by retarding the exothermic reaction to lower the exothermic temperature when the exothermic temperature exceeds an intended maximum exothermic temperature, and by suppressing an excessive exothermic reaction of the exothermic composition.

It has been found as a result that the heating principle of a disposable body warmer and the like is based on a heat generation occurring with the oxidation of a metal powder, and the rate of this oxidation, or exothermic reaction, is greatly influenced by the quantity of water in particular.

That is, to promote this oxidation, an appropriate degree of moisture is the key; the reaction is markedly retarded if moisture is too much or too little. A good balance between necessary moisture and air (oxygen) supply is said to maximize the rate of oxidation or exothermic reaction.

Too little moisture results in a shortage of moisture necessary for the reaction though air is sufficient. Too much moisture results in barrier layers of moisture to diminish air supply, thereby retarding the reaction.

Inventor has found that, where the exothermic composition includes a water absorber which, at above a predetermined temperature, releases adsorbed water to increase free moisture, and the free moisture forms barrier layers to diminish air supply and lower the exothermic temperature. With lowering of the exothermic temperature, the water absorber adsorbs the free moisture to eliminate the barrier layers, thereby increasing air supply. Thus, it has been found, the exothermic temperature maintains a certain value or rises and falls between a certain maximum temperature and minimum temperature, which has led to completion of the present invention.

SUMMARY OF THE INVENTION

Thus, the object of the present invention is to provide a method of controlling an exothermic reaction, using water, of an exothermic composition, the exothermic composition, an exothermic device and an application pad, in which the exothermic composition is enclosed in a container at least part of which is gas-permeable, and generates heat in the presence of air, the exothermic composition including a water absorber having a water absorptive ability reversibly variable with temperature variations, the water absorber releasing adsorbed water, at above a predetermined temperature, to increase free moisture, thereby retarding the exothermic reaction, and in which an extended use period is secured by suppressing an excessive exothermic reaction of the exothermic composition, and safety in use is enhanced when applied to a living body such as a human body.

In order to fulfill the above object, the present invention provides a method of controlling an exothermic reaction of an exothermic device, comprising enclosing an exothermic composition in a container at least part of which is gas-permeable, the exothermic composition generating heat in the presence of air; and mixing into the exothermic composition a water absorber having a water absorptive ability reversibly variable with temperature variations, the water absorber releasing adsorbed water, at above a predetermined temperature, to increase free moisture, thereby retarding the exothermic reaction.

The method of controlling the exothermic reaction of an exothermic device according to the present invention will be described in detail hereinafter.

The container used in the present invention is not limited to a particular configuration as long as the exothermic composition can be enclosed therein. Specifically, for example, a pouch or the like formed of an organic material may be used. It is necessary for the container to be gas-permeable at least in part thereof, in order to maintain the exothermic composition enclosed therein in continuous contact with air.

The exothermic composition, for example, generates heat in the presence of air. The exothermic composition has mixed therein a water absorber having a water absorptive ability reversibly variable with temperature variations, the water absorber releasing adsorbed water, at above a predetermined temperature, to increase free moisture, thereby retarding the exothermic reaction.

That is, the exothermic composition may comprise the exothermic composition according to the present invention described hereinafter.

In the present invention, the retardation of the exothermic reaction means that, at a high temperature above the predetermined temperature, the water absorber releases absorbed water to increase the quantity of free moisture, whereby the free moisture forms barrier layers to diminish the contact between iron powder and air, thereby lowering the reaction rate or temporarily or intermittently stopping the exothermic reaction.

Specifically, at a high temperature above the predetermined temperature, the water absorber releases absorbed water to increase the quantity of free moisture. As a result, in a predetermined range of temperature, e.g. approximately 43° C. when directly applied to a skin of the human body, the reaction may be retarded to lower the temperature to approximately 40° C. and maintain the temperature at this level.

Alternatively, at a high temperature and a low temperature, the water absorber may release adsorbed water or adsorb free moisture to vary the free moisture within the exothermic composition, to raise and lower the temperature within a proper range, e.g. a range between approximately 37 and 43° C.

In this case, no problem arises if the temperature during use may fall below 37° C. temporarily or intermittently.

In the present invention, with the decrease in the exothermic temperature resulting from the retardation of the exothermic reaction due to the release of adsorbed water from the water absorber, the water absorber may adsorb moisture to cause the exothermic reaction again.

The water absorber, for example, has a water absorptive ability reversibly variable with temperature variations, which releases adsorbed water, at above the predetermined temperature, to increase free moisture, thereby retarding the exothermic reaction.

That is, the water absorber is not limited to a particular type as long as its water absorptive ability is reversibly variable with temperature variations.

In the present invention, the water absorber, preferably, comprises a water-soluble cellulose ether, poly-N-vinylacetamide or the like which has a water absorptive ability reversibly variable with temperature variations.

Specific examples include water-soluble cellulose ethers such as methyl cellulose prepared by etherifying cellulose with the methoxyl group (Metolose SM15, Metolose SM25, Metolose SM400, Metolose SM4000 and so on manufactured by Shinetsu Kagaku Kogyo K. K.), hydroxypropyl methyl cellulose prepared by etherifying cellulose with the hydroxypropoxyl group (Metolose 60SH-50, Metolose 60SH-4000, Metolose 90SH-4000, Metolose 90SH-30000, Metolose 90SH-100000 and so on manufactured by Shinetsu Kagaku Kogyo K. K.), hydroxyethylmethyl cellulose prepared by etherifyng cellulose with the hydroxyethoxyl group (Metolose 60SH-50, Metolose 60SH-4000, Metolose 90SH-4000, Metolose 90SH-30000, Metolose 90SH-100000 and so on manufactured by Shinetsu Kagaku Kogyo K. K.), and carboxymethyl cellulose (hereinafter "CMC").

When an aqueous solution of the water-soluble cellulose ether is heated, the viscosity decreases until a predetermined temperature (thickening starting temperature) is reached. When the solution is further heated to a higher temperature, adsorbed water is released to increase viscosity and start gelation (this phenomenon being hereinafter referred to as heat gelatinization). The free moisture forms barrier layers to retard the exothermic reaction. When the gel is cooled, it adsorbs moisture to return to the original state.

That is, the water-soluble cellulose ether has such a property that, when heated to raise the exothermic temperature above a predetermined temperature, the ether becomes gelatinized while releasing adsorbed water to the ambient. When cooled, the gel adsorbs moisture to return to the original state. From a different point of view, this ether has a property that, at a high temperature, it releases adsorbed water to the ambient, and at a low temperature, it adsorbs free moisture from the ambient to enhance contact between iron powder and air.

Thus, by blending this water absorber into the exothermic composition, water adsorbed by the water absorber is released to the ambient when the exothermic temperature rises above the thickening starting temperature, to increase the quantity of free moisture around the iron powder. In other words, barrier layers of free moisture are formed around the iron powder to impair contact thereof with air, thereby retarding the exothermic reaction. With the retardation of the exothermic reaction of the exothermic composition, the temperature increase of the exothermic composition is stopped and thereafter the temperature begins to decrease. With this temperature decrease, the water absorber adsorbs the free moisture from the ambient to enhance the contact between iron powder and air.

The thickening starting temperature of the water-soluble cellulose ether is dependent on the type of etherifying substance, the rate of replacement, the molecular weight of cellulose, the concentration of solution when added in this form, the type and quantity (concentration) of an additive, if any, and the rates of temperature increase and temperature decrease. Thus, a maximum exothermic temperature may be determined, as desired, by selecting a type of etherifying substance, rate of replacement, molecular weight of cellulose, concentration of solution, type and quantity (concentration) of an additive, or by controlling the rates of temperature increase and temperature decrease by selecting a composition and use quantity of the exothermic composition.

The thickening starting temperature is 55° C. in the case of an aqueous solution of the above water-soluble cellulose ether (e.g. Metolose SM4000 manufactured by Shinetsu Kagaku Kogyo K. K.) in 2% by weight, without an additive, for example. Where sodium chloride (NaCl) or sodium carbonate ($Na_2CO_3 \cdot 10H_2O$) is added in 5% by weight, the thickening starting temperature is 40° C. When directly applied to the human body, Metolose SM4000 releases adsorbed water at below the safety temperature (about 43° C.) to suppress the exothermic reaction.

The thickening starting temperature of Metolose SM4000 is 45° C. where $Al_2(SO_4)_3 \cdot 18H_2O$ is added in 5% by weight. At this temperature, Metolose SM4000 releases adsorbed water around the iron powder to suppress the exothermic reaction.

The thickening starting temperature is 75° C. in the case of an aqueous solution of the water-soluble cellulose ether (e.g. Metolose 60SH-4000 manufactured by Shinetsu Kagaku Kogyo K. K.) in 2% by weight, without an additive, for example. Where sodium chloride (NaCl) is added in 5% by weight, the thickening starting temperature is 70° C. Where sodium carbonate ($Na_2CO_3 \cdot 10H_2O$) is added in 5% by weight, the thickening starting temperature is 45° C. At these temperatures, Metolose 60SH-4000 releases adsorbed water to the ambient to suppress the exothermic reaction.

The thickening starting temperature of Metolose 60SH-4000 is 50° C. where $Al_2(SO_4)_3 \cdot 18H_2O$ is added in 5% by weight. At this temperature, Metolose 60SH-4000 releases adsorbed water to increase the quantity of free moisture around the iron powder to suppress the exothermic reaction.

The thickening starting temperature is 85° C. in the case of an aqueous solution of the water-soluble cellulose ether (e.g. Metolose 90SH-4000 manufactured by Shinetsu Kagaku Kogyo K. K.) in 2% by weight, without an additive, for example. Where sodium chloride (NaCl) is added in 5% by weight, the thickening starting temperature is 60° C. Where sodium carbonate ($Na_2CO_3 \cdot 10H_2O$) is added in 5% by weight, the thickening starting temperature is 60° C. At this temperature, Metolose 90SH-4000 releases adsorbed water to increase the quantity of free moisture around the iron powder to suppress the exothermic reaction.

The thickening starting temperature of Metolose 90SH-4000 is 65° C. where $Al_2(SO_4)_3 \cdot 18H_2O$ is added in 5% by weight. At this temperature, Metolose 90SH-4000 releases adsorbed water to increase the quantity of free moisture around the iron powder to suppress the exothermic reaction.

Examples of additive for adjusting the thickening starting temperature of the above water absorber include, besides sodium chloride and sodium carbonate noted above, inorganic substances such as aluminum sulfate, lower alcohols such as ethanol, polyhydric alcohols such as polyethylene glycol and glycerin, and organic water retainers such as water absorptive polymers described hereinafter. The water-soluble cellulose ether may be used with an organic solvent since it still maintains the property to release adsorbed water at above the predetermined temperature, and adsorb free moisture when cooled. It is possible to facilitate or expedite manufacture where the water-soluble cellulose ether is dissolved in such an organic solvent, particularly in a mixed solvent which enables variations in viscosity based on mixing ratios of the solvent.

Where plural types of water-soluble cellulose ethers are used, a compounding ratio may be selected to control viscosity increasing rate and maximum exothermic temperature after a start of thickening. Thus, the maximum exothermic temperature may be limited to or below a predetermined temperature, or the time in which the predetermined temperature is exceeded may be limited within a safety period.

At the predetermined temperature or above, the adsorbed water released from the water absorber remains free around unreacted iron powder to form barrier layers to lower the exothermic temperature. When the exothermic temperature lowers, the free moisture around the iron powder is adsorbed to enhance the contact between iron powder and air, thereby promoting the exothermic reaction again.

That is, the exothermic reaction is promoted again (hereinafter referred to as reactivation) when the exothermic temperature lowers and the free moisture around the iron powder is adsorbed to enhance the contact between iron powder and air. The rate of the exothermic reaction is dependent on the quantity of moisture adsorbed by the water absorber per unit time (hereinafter referred to as unit time adsorption). In the event of a large unit time adsorption, the exothermic reaction is rapidly reactivated whereby the exothermic temperature rises as at the initial stage. With a small unit time adsorption, the exothermic reaction is reactivated only slowly, whereby the exothermic temperature increases gradually. When unit time adsorption is even less, the exothermic temperature remains constant or decreases due to a balance with heat radiation to the ambient.

Where the quantity of unreacted iron powder is small in relation to the quantity of moisture adsorbed by the water absorber, the reactivation of the exothermic reaction is dependent on the quantity of unreacted iron powder.

In the case of the water-soluble cellulose ether, the unit time adsorption is dependent on the type of etherifying substance, the rate of replacement, the molecular weight of cellulose and so on. Thus, a desired water absorber, and hence desired reactivation, may be realized by selecting a type of etherifying substance, rate of replacement, molecular weight of cellulose and the like.

The poly-N-vinylacetamide noted above is obtained by radical polymerization of N-vinylacetamide, and may have a straight chain structure soluble in water, or a bridged structure insoluble in water. The insoluble poly-N-vinylacetamide includes microgel acting as a gelling agent based on a difference in crosslink density. Specifically, it may comprise, for example, one or a mixture or two or more of N-vinylacetamide-sodium acrylate copolymer (GE-167 manufactured by Showa Denko K. K), N-vinylacetamide homopolymer (GE-191 manufactured by Showa Denko K. K.) and N-vinylacetamide crosslinked compound (microgel) (GX-205 manufactured by Showa Denko K. K.). These compounds may be treated or combined with a surface active agent to improve hydrophilic property. These compounds have a water absorptive ability reversibly variable with variations of humidity.

Only one type of the water-soluble cellulose ether noted above may be used. Instead, two or more water-soluble cellulose ethers may be used, or one, two or more water-soluble cellulose ethers may be combined with a different water retainer, to determine a temperature range for use as desired.

As is the water-soluble cellulose ether, only one poly-N-vinylacetamide may be used, or a mixture of poly-N-vinylacetamide and water-soluble cellulose ether may be used. In addition, these may be combined with a different water retainer, to determine a temperature range for use as desired.

The different water retainer may be an inorganic water retainer and/or an organic water retainer. Particularly preferred is an organic water retainer or a mixture of an organic water retainer and an inorganic water retainer which has high water retention to eliminate stickiness of the exothermic composition for handling convenience.

That is, it is desirable to blend a water retainer comprising a water absorptive polymer into the exothermic composition, besides the water-soluble cellulose ether for holding water. The water absorbed by the water retainer may be released gradually to maintain a fixed exothermic temperature or maintain the exothermic temperature relatively steadily.

The inorganic water retainer includes, for example, pearlite, cristobalite, vermiculite, a siliceous porous substance, calcium silicate, and silica powder.

The organic water retainer is not limited to a particular substance as long as it is organic and water retentive. Preferably, its water retaining capacity is at least 15 times its weight, desirably 20 times or more.

Specific examples include a water absorptive polymer, other than the water-soluble cellulose ether and consisting of one or a combination of two or more of starch-polyacrylonitrile copolymer disclosed in Japanese Patent Publication No. 49-43395, crosslinked polyalkylene-oxide disclosed in Japanese Patent Publication No. 51-39672, vinylesterethylene unsaturated carboxylic copolymer saponificate disclosed in Japanese Patent Publication No. 53-13495, self-crosslinked polyacrylic salt obtained by reverse phase suspension polymerization which is disclosed in Japanese Patent Publication No. 54-20093, a reaction product of polyvinylalcohol polymer and cyclic anhydride disclosed in Japanese Patent Laying-Open Publication No. 54-20093, polyacrylic salt crosslink compound disclosed in Japanese Patent Laying-Open Publication No. 59-84305, sodium polyacrylate or CMC, polyvinyl alcohol, polyvinyl pyrrolidone, gum arabic, hydroxyethyl cellulose, methyl cellulose, sodium alginate, pectin, carboxyvinyl polymer, acrylsulfonic acid high polymer (e.g. CS-6HS manufactured by Nihon Shokubai K. K.), gelatin, and polyethylene oxide; or wood flour.

A commercially available product may be used as the water absorptive polymer. Examples thereof include Sanwet IM-1000, Sanwet IM-300MS and Sanwet IM-1000MPS manufactured by Sanyo Kasei IC K., Aquakeep 4S and Aquakeep 4SH manufactured by Seitetsu Kagaku K. K, Sumikagel NP-1020, Sumikagel NP-1040, Sumikagel SP-520 and Sumikagel N-1040 manufactured by Sumitomo Kagaku K. K., KI Gel 201-K and KE Gel 201-F2 manufactured by Kurare K. K., and Arasoap 800 and Arasoap 800F manufactured by Arakawa Kagaku K. K.

Particularly preferred among these commercially available water absorptive polymers, are Sanwet IM-300MS and Sanwet IM-1000MPS manufactured by Sanyo Kasei K. K., Sumikagel NP-1020 and Sumikagel NP-1040 manufactured by Sumitomo Kagaku K. K., and Arasoap 800F manufactured by Arakawa Kagaku K. K. which are highly water absorptive, and excellent in integrity of the adhesive layer, showing no loosening thereof layers when heated.

The present invention is not limited in application, but may be applied to the exothermic device, the heating type application pad described hereinafter, as long as the exothermic composition according to the present invention is utilized.

Other organic water retainers include carrageenan, which is the most common, a combination of carrageenan, locust beam gum, potassium chloride and CMC and a combination of copper carrageenan and iota carrageenan, which are basic examples, a combination of carrageenan, agar, locust bean gum, polyvinyl alcohol, hydroxypropyl cellulose, gum guar and gum arabic, and a combination of carrageenan and a surface active agent.

In the method of controlling an exothermic reaction of an exothermic device according to the present invention, as noted hereinbefore, an exothermic composition enclosed in a container at least part of which is gas-permeable has a water absorber having a water absorptive ability reversibly variable with temperature variations. The water absorber releases adsorbed water at above a predetermined temperature. The water released is adsorbed by iron powder to form barrier layers, thereby suppressing contact between iron powder and air to retard the exothermic reaction. Thus, the exothermic temperature may be limited to the predetermined temperature, e.g. a safety temperature when applied to the human body, or the period in which the safety temperature is exceeded may be shortened to a safety period, even in the event of variations in gas permeability, water-vapor permeability and the exothermic composition or a high ambient temperature.

The heating principle of a disposable body warmer and the like is based on a heat generation occurring with the oxidation of a metal powder, and the rate of this oxidation, or exothermic reaction, is greatly influenced by the quantity of water in particular.

That is, to promote this oxidation, an appropriate degree of moisture is the key; the reaction is markedly retarded if moisture is too much or too little. A good balance between necessary moisture and air (oxygen) supply is said to maximize the rate of oxidation or exothermic reaction.

Too little moisture results in a shortage of moisture necessary for the reaction though air is sufficient. Too much moisture results in barrier layers of moisture to diminish air supply, thereby retarding the reaction.

In the present invention, the exothermic composition includes a water absorber which, at above a predetermined temperature, releases adsorbed water to increase free moisture. The free moisture form barrier layers to diminish air supply and lower exothermic temperature. With lowering of the exothermic temperature, the water absorber adsorbs the free moisture to eliminate the barrier layers, thereby increasing air supply. Thus, the exothermic temperature maintains a certain value or rises and falls between a certain maximum temperature and minimum temperature.

In the method of controlling an exothermic reaction of an exothermic composition according to the present invention, the water absorber releases adsorbed water, at above a predetermined temperature, to retard the exothermic reaction, thereby lowering the exothermic temperature. With the decrease in the exothermic temperature, the water absorber may adsorb ambient moisture to reactivate the exothermic reaction. In this case, the increase in the exothermic temperature is suppressed by the retardation of the exothermic reaction. When, subsequently, the temperature decreases to a predetermined temperature, the exothermic reaction is reactivated. Thus, the exothermic temperature may be lowered slowly from the predetermined temperature, may be maintained at the predetermined temperature or may be raised again from the predetermined temperature.

When raising the exothermic temperature again from the predetermined temperature, a repetition may be made of the temperature limitation by the release of water from the water absorber and the temperature increase by the adsorption of free moisture by the water absorber.

Further, in the method of controlling temperature of an exothermic composition according to the present invention, the exothermic composition may further include a water retainer comprising a polymer having high water absorptivity. The water retainer may gradually release absorbed water, whereby the exothermic composition may maintain a fixed level of minimum exothermic temperature over a long period of time. The temperature decrease by the retardation of the exothermic reaction and the temperature increase by the reactivation of the exothermic reaction may be repeated plural times.

The temperature control method based on the water retainer utilizes the property of the water retainer to vary its water absorbing ability with temperature variations. Thus, temperature may be controlled regardless of variations in ambient temperature, gas permeability, water-vapor permeability and the exothermic composition.

In the temperature control method of the present invention, where the exothermic composition further includes a water retainer comprising a polymer having high water absorptivity, the water retainer gradually releasing absorbed water, the water released from the water retainer maintains the rate of the exothermic reaction of the exothermic composition at or above a fixed level over a long period of time. The temperature variations caused by the water retainer may be repeated an increased number of times, and the temperature decrease may be switched to the temperature increase at an increased temperature.

In the temperature control method of the present invention, where the water absorber comprises a water-soluble cellulose ether, temperature characteristics such as a maximum exothermic temperature, minimum exothermic temperature, temperature increase rate, temperature decrease rate, temperature variation cycle and exothermic temperature difference may be determined as desired and with ease by selecting a type of etherifyng substance, rate of replacement, molecular weight of cellulose, mixing ratio or concentration of the exothermic composition, type and concentration of an additive, or use quantity of the exothermic composition.

Consequently, the present invention may suitably be applied to any fields utilizing the heat derived from the exothermic reaction of the exothermic composition, such as a heat treating device or application pad applicable to the human body.

In the method of controlling an exothermic reaction of an exothermic device according to the present invention, as described above, the exothermic composition has blended therein a water absorber having a water absorptive ability variable with temperature variations. The water absorber releases adsorbed water at above a predetermined temperature. The released water is adsorbed by iron powder to form barrier layers therearound, thereby suppressing contact between iron powder and air to retard the exothermic reaction. Thus, the exothermic temperature may be limited to the predetermined temperature, e.g. a safety temperature not inflicting a low-temperature burn when applied to the human body, or the period in which the safety temperature is exceeded may be shortened or to a safety period, even in the event of variations in gas permeability, water-vapor permeability and the exothermic composition or a high ambient temperature, thereby securing safety when applied to a living body such as human body.

That is, in the method of controlling temperature of an exothermic device according to the present invention, the exothermic composition has blended therein a water absorber having a water absorptive ability reversibly variable with temperature variations. When the exothermic composition exceeds a predetermined temperature after start of a exothermic reaction, the water absorber releases adsorbed water to retard the exothermic reaction. Thus, an abnormal temperature increase is suppressed regardless of the gas permeability and water-vapor permeability of a container such as a pouch and regardless of ambient temperature. The exothermic temperature may be limited to a safety temperature not inflicting a low-temperature burn when applied to the human body, or the period in which the safety temperature is exceeded may be limited or to a safety period not inflicting a low-temperature burn. Thus, the exothermic composition may be applied directly to a surface of a living body such as human body, and may be used during a period of sleep.

In the method of controlling temperature of an exothermic device according to the present invention, with the decrease in the exothermic temperature resulting from the retardation of the exothermic reaction due to the release of adsorbed water from the water absorber, the water absorber may adsorb moisture to reactivate the exothermic reaction again. When the exothermic temperature exceeds a predetermined temperature, the exothermic temperature is lowered to the predetermined temperature (substantially fixed temperature) for producing a heating effect, or raised again to repeat increase and decrease of the exothermic temperature. This reduces an unreacted part of the exothermic composition to enhance safety of waste disposal, to assure effective use of the exothermic composition and to increase the heating effect. A type of massaging effect may be obtained particularly when the exothermic temperature is repeatedly raised and lowered.

In the method of controlling temperature of an exothermic composition according to the present invention, the exothermic composition may further include a water retainer for gradually release absorbed water. Then, the exothermic composition may maintain a fixed level of exothermic temperature over a long period of time. The temperature decrease by the retardation of the exothermic reaction and the temperature increase by the reactivation of the exothermic reaction may be repeated plural times. Such temperature variations give variations in temperature stimuli to produce a type of massaging effect, and avoid an excessive absorption of skin absorbable medication due to high temperature, and an insufficient absorption of skin absorbable medication due to low temperature.

In the temperature control method of the present invention, where the water absorber comprises a water-soluble cellulose ether, temperature characteristics such as a maximum exothermic temperature, minimum exothermic temperature, temperature increase rate, temperature decrease rate, temperature variation cycle and exothermic temperature difference may be determined as desired and with ease by selecting a type of etherifying substance, rate of replacement, molecular weight of cellulose, mixing ratio or concentration of the exothermic composition, type and concentration of an additive, or use quantity of the exothermic composition.

Consequently, the present invention may suitably be applied to any fields utilizing the heat derived from the exothermic reaction of the exothermic composition, such as a heat treating device or application pad applicable to the human body. Moreover, the invention precludes excessive heating to enable a long period of use.

In another aspect of the present invention, an exothermic composition comprises, as essential components thereof, a metal powder, a metallic chloride, water, and a water absorber having a water absorptive ability reversibly variable with temperature variations due to an exothermic reaction.

The exothermic composition according to the present invention will particularly be described hereinafter.

The exothermic composition according to the present invention is not limited to a particular composition as long as it is an exothermic composition including water as an essential component thereof, generating heat through contact with air, and also including a water absorber having a water absorptive ability reversibly variable with temperature variations.

That is, the most salient characteristic of the exothermic composition according to the present invention lies in inclusion of a water absorber having a water absorptive ability reversibly variable with temperature variations.

Specifically, the exothermic composition comprises, as essential components thereof, a metal powder such as iron powder, a metallic chloride, water, and a water absorber having a water absorptive ability reversibly variable with temperature variations, and may further comprise a catalyst such as activated carbon or carbon black (hereinafter referred to as carbon component) for promoting the reaction, a pH regulator such as sodium tripolyphosphate, a water retainer, or an exothermic reaction auxiliary or surface active agent for promoting the exothermic reaction.

The water absorber used in the present invention is not limited to a particular type as long as its water absorptive ability is reversibly variable with temperature variations.

Specific examples include a water-soluble cellulose ether, CMC and poly-N-vinylacetamide. Other examples are listed in the description of the method of controlling the exothermic reaction of the exothermic composition according to the present invention, and will not be described again.

A water retainer may be used in the present invention, which may be an inorganic water retainer and/or inorganic water retainer. Specific examples are listed in the description of the method of controlling the exothermic reaction of the exothermic composition according to the present invention, and will not be described again.

A particularly preferred water retainer is a water absorptive polymer other than the water-soluble cellulose ether, which has high water retentivity and exhibits excellent water retention even when used in a small quantity. Specific examples are listed in the description of the method of controlling the exothermic reaction of the exothermic composition according to the present invention, and will not be described again.

Specific compounding examples of the exothermic composition according to the present invention are not easy to cite since required temperature is variable with use. It is desirable to meet varied temperature requirements by varying the water-vapor permeability of the gas-permeable pouch described hereinafter, and mixing ratio for the exothermic composition. Specifically, for example, a preferred mixing ratio is iron powder in 25 to 75% by weight, carbon component in 1 to 15% by weight, metallic chloride in 1 to 10% by weight, water in 10 to 55% by weight, and water absorber in 0.5 to 35% by weight. A preferred quantity of water retainer added as necessary is 1 to 20% by weight.

The metallic chloride may be a chloride of an alkali metal such as sodium chloride or potassium chloride, or a chloride of an alkali earth metal such as calcium chloride or magnesium chloride.

The water absorber used in the present invention is not limited to a particular type as long as its water absorptive ability is reversibly variable with temperature variations. Specific examples are listed in the description of the method of controlling the exothermic reaction of the exothermic composition according to the present invention, and will not be described again.

The exothermic composition according to the present invention includes a metal powder, particularly iron powder, a metal chloride, water, and a water absorber having a water absorptive ability reversibly variable with temperature variations. Therefore, regardless of variations in ambient temperature, gas permeability, water-vapor permeability and the exothermic composition, the water absorber releases adsorbed water at above a predetermined temperature, to retard the exothermic reaction reliably. Since the method of controlling temperature of the exothermic composition according to the present invention may be implemented, the exothermic temperature may be limited to a predetermined temperature, e.g. a safety temperature when applied to the human body, or the period in which the safety temperature is exceeded may be limited to a safety period.

In the exothermic composition according to the present invention, with the decrease in the exothermic temperature resulting from the retardation of the exothermic reaction due to the release of adsorbed water from the water absorber, the water absorber may adsorb moisture to reactivate the exothermic reaction again. When the exothermic temperature exceeds a predetermined temperature, the exothermic temperature may be lowered. Or after the exothermic temperature exceeds the predetermined temperature and the exothermic temperature is lowered, the exothermic temperature may be maintained at a fixed safe temperature or may be raised again. Particularly where the exothermic temperature is raised again to the predetermined temperature, the exothermic temperature may be repeatedly raised and lowered within a predetermined range.

Where the exothermic composition further includes a water retainer comprising a polymer having high water absorptivity, the water retainer gradually releasing absorbed water, the water released from the water retainer maintains the rate of the exothermic reaction of the exothermic composition at or above a fixed level over a long period of time. The temperature variations caused by the water retainer may be repeated an increased number of times, and the temperature decrease may be switched to the temperature increase at an increased temperature.

Where the exothermic composition further includes an exothermic auxiliary for stabilizing the exothermic temperature, the exothermic reaction may be performed steadily to smooth variations in the exothermic temperature.

In addition, in the exothermic composition according to the present invention, where the water absorber comprises a water-soluble cellulose ether, temperature characteristics such as a maximum exothermic temperature, minimum exothermic temperature, temperature increase rate, temperature decrease rate, temperature variation cycle and exothermic temperature difference may be determined as desired and with ease by selecting a type of etherifying substance, rate of replacement, molecular weight of cellulose, mixing ratio or concentration of the exothermic composition, type and concentration of an additive, or use quantity of the exothermic composition.

The exothermic composition according to the present invention includes a metal powder, particularly iron powder, a metal chloride, water, and a water absorber having a water absorptive ability reversibly variable with temperature variations. Therefore, regardless of the gas permeability and water-vapor permeability of the container such as a pouch, variations in the exothermic composition and ambient temperature, the water absorber in the exothermic composition releases adsorbed water when the exothermic reaction proceeds to excess and exceeds a predetermined temperature, to retard the exothermic reaction reliably. Consequently, the exothermic temperature may be limited to a predetermined temperature, e.g. a safety temperature (43° C.) not to inflict a low-temperature burn when applied to the human body, or the period in which the safety temperature is exceeded may be limited to a safety period. Thus, the exothermic composition may be applied directly to a surface of a living body such as human body, and may be used during a period of sleep. A heating effect may be produced with increased safety and quality.

In the exothermic composition according to the present invention, the exothermic reaction is retarded when the predetermined temperature is reached. When the exothermic temperature decreases to the predetermined temperature as a result of the retardation of the exothermic reaction, the water absorber adsorbs the free moisture from around the metal powder to eliminate the barrier layers, thereby reactivating the exothermic reaction. Thus, the exothermic temperature may be maintained at the predetermined temperature, or may be raised and lowered within a certain range. This reduces an unreacted part of the exothermic composition to enhance safety of waste disposal, to assure effective use of the exothermic composition and to increase the heating effect. A type of massaging effect may be obtained particularly when the exothermic temperature is repeatedly raised and lowered.

Where the exothermic composition according to the present invention further includes a water retainer for holding water, the water retainer gradually releases water to maintain the rate of the exothermic reaction of the exothermic composition at or above a fixed level over a long period of time. The temperature variations may be repeated an increased number of times. Consequently, a required heating effect is secured and a type of massaging effect is promoted by the repetition of temperature variation.

In the exothermic composition according to the present invention, the water absorber releases adsorbed water, at above a predetermined temperature, to retard the exothermic reaction. With a decrease in the exothermic temperature, the water absorber adsorbs free moisture from around the metal powder to reactivate the exothermic reaction. Thus, it is possible to slow down the decrease in the exothermic temperature, to maintain the exothermic temperature at the predetermined temperature, or to raise the exothermic temperature again. The exothermic temperature may be repeatedly raised and lowered within a predetermined range particularly where the exothermic temperature is raised again to the predetermined temperature.

Where the exothermic composition according to the present invention further includes, besides the water-soluble cellulose ether, a water retainer comprising a polymer having high water absorptivity, the water retainer gradually releasing absorbed water, the exothermic reaction may be maintained at or above a fixed level over a long period of time. The temperature variations may be repeated an increased number of times, and the temperature decrease may advantageously be switched to the temperature increase at an increased temperature.

Where the exothermic composition further includes an exothermic auxiliary for stabilizing the exothermic temperature, the exothermic reaction may advantageously be performed steadily to smooth variations in the exothermic temperature.

In addition, in the exothermic composition according to the present invention, where the water absorber comprises a water-soluble cellulose ether, temperature characteristics such as a maximum exothermic temperature, minimum exothermic temperature, temperature increase rate, temperature decrease rate, temperature variation cycle and exothermic temperature difference may be determined as desired and with ease by selecting a type of etherifying substance, rate of replacement, molecular weight of cellulose, mixing ratio or concentration of the exothermic composition, type and concentration of an additive, or use quantity of the exothermic composition.

In order to fulfill the object noted hereinbefore, the present invention provides also an exothermic device comprising the above exothermic composition according to the present invention enclosed in a flat pouch having at least one gas-permeable surface.

The exothermic device according to the present invention will be described in detail hereinafter.

The pouch used in the present invention is not limited to any particular type as long as it can enclose the exothermic composition according to the present invention and has at least one gas-permeable surface.

The pouch is formed flat to contact a required area of a curves surface of a living body such as the human body to which the pouch is applied, and to minimize a heat transfer path from the exothermic composition to the surface of the living body.

Preferably, the pouch is formed of a soft material such as a plastic film, woven or nonwoven fabric (including paper)

or the like to be flat to follow movement and a complicated curved surface of the living body.

The exothermic device according to the present invention may be formed by injecting or inserting the exothermic composition into a flat pouch formed of a film and having at least one gas-permeable surface, and sealing open sides thereof. The type of sealing may be side sealing, two-side sealing, three-side sealing, envelope type or mid-joint sealing. The pouch is often sealed by heat sealing. However, where opposite films or sheets are formed of a material not fit for heat sealing, a hot melt type adhesive or hot melt adhesive film, or a paste, may be interposed between the opposite plastic films.

At least one surface of the flat pouch may be made gas-permeable, for example, by punching a gastight pouch to form numerous pores therein. To simplify a pouch manufacturing process, one or both surfaces of the pouch may be formed of a gas-permeable plastic film obtained by a drawing process, woven or nonwoven fabric (including paper), or a combination thereof (hereinafter referred to as gas-permeable film).

The material for the gas-permeable film is not limited to any particular material, but may be a known material conventionally used for a pouch which encloses a exothermic composition. Usable materials include, for example, paper, polyethylene, polypropylene, polyamide, polyester, polyvinyl chloride, polyvinylidene chloride, polyurethane, polystyrene, saponified ethylene-vinyle acetate copolymer, ethylene-vinyle acetate copolymer, natural rubber, reclaimed rubber and synthetic rubber.

The gas permeability of the gas-permeable film influences control of the exothermic temperature and heating time of the exothermic device. Conventionally, it is preferred to control the gas permeability of the film by means of water-vapor permeability to effect a particularly strict temperature control of the exothermic device in order to obtain an effective heating effect and to secure safety by avoiding a low-temperature burn.

In the present invention, however, strict setting of water-vapor permeability is unnecessary since the temperature may be lowered by retarding the exothermic reaction at above a predetermined temperature. Specifically, though this depends on use, the invention may employ a gas-permeable film having a water-vapor permeability at 50 to 5000 g/m$^2$·24 hr, preferably 50 to 2500 g/m$^2$·24 hr by the ASTM method (E-96-80D method). Consequently, heat is generated at a desirable temperature with a good balance between heat generation based on a reaction between oxygen in the air and the exothermic composition, and heat absorption and radiation to the ambient based on water evapotranspiration.

Thus, in the present invention, the water absorber controls the exothermic temperature by releasing adsorbed water and adsorbing free moisture from around the metal powder. It is therefore unnecessary to control water-vapor permeability (quantity) strictly. That is, the invention may use a gas-permeable film having a wide range of water-vapor permeability (quantity). The gas-permeable film may be obtained at low cost.

In manufacturing an exothermic device for application to the human body, the water-vapor permeability of the gas-permeable film specified by the ASTM method (E-96-80D method) must be strictly controlled to a narrow range of variation at plus/minus 5 to 10% of the standard value, or plus/minus 20 to 35% of the standard value at most, unless a temperature control is provided as in the present invention.

Where the water-vapor permeability of the gas-permeable film is strictly controlled as above, the gas-permeable film must be manufactured with strict specifications to lower yield and raise manufacturing cost. Even if manufacturing specifications are made strict, the water-vapor permeability of the gas-permeable film used is not necessarily controlled to be within the above range. Some pouches are formed of gas-permeable films having water-vapor permeability outside the above range, or variations could occur in the exothermic composition, or in environmental factors such as ambient temperature and humidity.

As a result, variations may occur in the maximum exothermic temperature to exceed a predetermined temperature set according to use.

Specifically, when applied to the human body, for example, an exothermic device may inflict a low-temperature burn, causing blisters or erythema. The exothermic device according to the present invention is manufactured using the exothermic composition according to the present invention. This exothermic composition includes a water absorber having a water absorptive ability reversibly variable with temperature variations. The water absorber releases absorbed water at a high temperature. The water acts as barrier layers to suppress contact between metal powder and air, thereby retarding the exothermic reaction. Even if some pouches are formed of gas-permeable films having water-vapor permeability outside the above-noted range, a very high degree of safety is secured, and excessive heating is suppressed to provide a prolonged heating period.

The water-vapor permeability of the gas-permeable film less than 50 g/m$^2$·24 hr results in little heating and does not provide a sufficient heating effect. The water-vapor permeability exceeding 5000 g/m$^2$·24 hr may result in an exothermic temperature above 70° C. When 70° C. is exceeded, the exothermic reaction is retarded to lower the exothermic temperature. With the temperature decrease, moisture is absorbed to raise the temperature again, which may exceed 70° C. again. When 70° C. is exceeded repeatedly, it is undesirable that a low-temperature burn may be caused even if the device is applied to underwear.

Thus, preferably, the water-vapor permeability of the gas-permeable film is in the range of 50 to 2500 g/m$^2$·24 hr in particular. The water-vapor permeability of the gas-permeable film less than 50 g/m$^2$·24 hr results in little heating and does not provide a sufficient heating effect. The water-vapor permeability exceeding 2500 g/m$^2$·24 hr may result in an exothermic temperature above 45° C. When 45° C. is exceeded, the exothermic reaction is retarded to lower the exothermic temperature. With the temperature decrease, moisture is absorbed to raise the temperature again, which may exceed 45° C. again. When 45° C. is exceeded repeatedly, it is undesirable that a low-temperature burn may be caused if the device is applied directly to the skin.

In the ASTM method (E-96-80D method), 20 ml of pure water is placed in a cup 6.18 cm in inside diameter and 1.5 cm in height. After a gas-permeable film is placed over an upper plane of the cup and fixed with wax, the cup is kept in a constant temperature (32.2° C.) and constant humidity (50%) condition. Then, a reduction in the quantity of water in the cup is measured, and this reduction, i.e. a quantity of water released through evapotranspiration is converted to [gim$^2$·24 hr].

Where the pouch of the exothermic device has only one surface formed of a gas-permeable film, the other surface is formed of a gas-tight film or sheet. Materials usable therefor include, for example, paper, polyethylene, polypropylene, polyamide, polyester, polyvinyl chloride, polyvinylidene chloride, polyurethane, polystyrene, saponified ethylene-vinyle acetate copolymer, ethylene-vinyl acetate copolymer, natural rubber, reclaimed rubber and synthetic rubber.

To increase the strength of this pouch, a gas-permeable film such as of woven or nonwoven fabric may be used. The gas-permeable film of woven or nonwoven fabric may form at least one surface of the pouch. The gas-permeable film of woven or nonwoven fabric may be laminated on a different gas-permeable film or gas-barrier film.

However, if the surface formed by the gas-permeable film of woven or nonwoven fabric acts as the gas-permeable surface, the water-vapor permeability of this gas-permeable surface should preferably be within the range of 50 to 2500 $g/m^2 \cdot 24$ hr by the ASTM method (E-96-80D method), in order to secure both a heating effect or heat stimulating effect and safety.

Fibers for forming the gas-permeable film of woven or nonwoven fabric may be one or a combination of synthetic fibers such as nylon, vinylon, polyester, rayon, acetate, acryl, polyethylene, polypropylene and polyvinyl chloride, and natural fibers such as pulp, cotton, hemp, silk and animal hair.

The exothermic device according to the present invention may include, enclosed in the pouch, a ceramic material radiating far infrared rays (far infrared radiator). Alternatively, the pouch may carry a far infrared radiator mixed into one surface thereof. This is preferable in that the far infrared radiation promotes the heating effect.

The exothermic device according to the present invention comprises the exothermic composition according to the present invention enclosed in a flat pouch having at least one gas-permeable surface. Air entering the pouch to cause a chemical reaction (oxidation) with the metal powder, particularly iron powder, the metallic chloride and water. When the resulting heat raises the temperature of the exothermic composition above a predetermined temperature, the water absorber releases adsorbed water regardless of ambient temperature, gas permeability, water-vapor permeability and variations in the exothermic composition. This forms barrier layers of free moisture around the metal powder to impair contact between metal powder and air, thereby retarding the exothermic reaction. Consequently, the exothermic temperature is prevented from increasing to a predetermined temperature, i.e. a safety temperature when the device is applied to the human body. Even if the safety temperature is exceeded, the heating time is limited to a safety period to enhance safety.

When the exothermic temperature decreases as a result of the retardation of the exothermic reaction, the water absorber adsorbs the free moisture to reactivate the exothermic reaction of water, air (oxygen), iron powder and metallic chloride. Thus, by retarding the decrease of the exothermic temperature, the predetermined temperature may be maintained. The temperature may be raised again to repeat temperature increase and decrease below a limited maximum exothermic temperature.

Where the exothermic device includes a far infrared radiator contained in the exothermic composition, far infrared rays generated with the exothermic reaction promote the heating effect.

The exothermic device according to the present invention comprises the exothermic composition according to the present invention enclosed in a flat pouch having at least one gas-permeable surface. Air entering the pouch to cause a chemical reaction with the metal powder, metallic chloride and water. When the resulting heat raises the temperature of the water absorber above a predetermined temperature, the water absorber releases adsorbed water to form barrier layers of released water around the metal powder to retard the exothermic reaction. Thus, regardless of gas permeability, water-vapor permeability, variations in the exothermic composition, and ambient temperature, the exothermic temperature is limited to a safety temperature, or the period in which the safety temperature is exceeded is limited to a safety period. The exothermic device may be applied directly to a surface of a living body such as human body, and may be used during a period of sleep.

When the exothermic temperature decreases as a result of the retardation of the exothermic reaction, the water absorber adsorbs the free moisture from around the metal powder to reactivate the exothermic reaction of water, air, metallic chloride and iron powder. This retards the decrease of the exothermic temperature, maintains the exothermic temperature at the predetermined temperature, or repeatedly raise and lower the temperature within a predetermined range. As a result, an unreacted part of the exothermic composition is reduced to enhance safety of waste disposal, assure effective use of the exothermic composition and to increase the heating effect. A type of massaging effect may be obtained particularly when the exothermic temperature is repeatedly raised and lowered.

In the exothermic device according to the present invention, the exothermic composition may further include a water retainer for gradually release absorbed water over a long period of time. Then, the exothermic composition may maintain a fixed level of exothermic temperature over a long period of time. The temperature decrease by the retardation of the exothermic reaction and the temperature increase by the reactivation of the exothermic reaction may be repeated an increased number of times.

In order to fulfill the object noted hereinbefore, the present invention provides also an application pad comprising the exothermic device according to the present invention, and an adhesive layer formed on one surface of the pouch of the exothermic device.

The application pad according to the present invention will be described in detail hereinafter.

The adhesive layer used in the present invention is not limited to any particular type as long as it can be applied directly to a human skin or to underwear or a sock to maintain the application pad in a location of application.

The adhesive layer may be a layer formed of an adhesive, or a layer formed of a compress to produce a hot compress effect regardless of presence of moisture.

The adhesive is not limited as long as it is a high polymer material having adhesive property. The invention may use various types of rubber adhesives and acrylic adhesives widely used to date as adhesives of application pads. A hot-melt type adhesive may also be used.

The adhesive may be a combination of two or more adhesives.

The hot-melt adhesive means an adhesive containing a hot-melt type high polymer. Examples of the hot-melt type high polymers include A-B-A type block copolymer, saturated polyester high polymer, acrylic high polymer, urethane high polymer, polyamide high polymer, polyamide high polymer, polyorefine high polymer, and polyorefine copolymer, modifications of these materials, and a mixture of two or more of these materials.

The modifications are those hot-melt high polymers part of which is replaced by other components in order to improve their properties such as tackiness or stability.

In A-B-A type block copolymer, A block is a monovinyl replaced aromatic compound such as styrene, methylstyrene, which is an inelastic polymer block, and B block is an elastic polymer block of conjugate diene such as butadiene or isoprene. Specific examples include styrene-butadiene-styrene block copolymer, and styrene-isoprene-styrene block copolymer, and a mixture thereof.

Commercially available A-B-A type block copolymers include Califlex TR-1101, Califlex TR-1107 and Califlex TR-1111 manufactured by Shell Chemicals, and Solprene 418 manufactured by Phillip Petroleum.

The hot-melt adhesive used in the present invention is not limited as long as it contains a hot-melt high polymer.

Thus, the adhesive may also include, for example, another adhesive, a tackifier, age resistor, filler, tackiness adjuster, tackiness improver, coloring agent, antifoaming agent, thickener, fungicide, antibacterial agent, sterilizer, deodorant, and so on.

In particular, adhesive strength is an important characteristic of the above adhesive, and this may easily be controlled by compounding the hot-melt high polymer with a tackifier such as an alicyclic petroleum resin.

The alicyclic petroleum resin is a petroleum resin having a cyclic skeleton. Specific examples include rosin, dehydrogenated rosin, glycerin esters of dehydrogenated rosin, glycerin esters of gum rosin, hydrogenated rosin, methylesters of hydrogenated rosin, glycerin esters of hydrogenated rosin, pentaerythritrosins of hydrogenated rosin, polymerized rosin, glycerin esters of polymerized rosin, coumarone-indene resin, hydrogenated petroleum resin, maleic anhydride modified resin, rosin derivatives, $C_5$ petroleum resin. These are used alone or in combination with others.

Commercially available products of the alicyclic petroleum resin include, for example, Alcon P-100 and Alcon P-125 manufactured by Arakawa Kagaku, Clayton manufactured by Nihon Zeon, and Escorets 3000 manufactured by Exon.

Where a tacifier is used, a softener also should preferably be added to soften the hot-melt high polymer dissolution or dispersion, and exhibit appropriate stiffness, softness and tackiness.

Examples of such softener include coconut oil, caster oil, olive oil, tsubaki oil, almond oil, parsic oil, peanut oil, sesame oil, mink oil, cotton seed oil, corn oil, safflower oil, olein oil, and liquid paraffin.

For a specific hot-melt adhesive, it is preferable to take into account adhesion to the skin, tackiness, comfort of use, and separation from the skin. From this point of view, a recommended adhesive includes a hot-melt high polymer in 5 to 40 parts by weight, alicyclic petroleum resin in 5 to 55 parts by weight, and softener in 5 to 55 parts by weight, and particularly recommended is an adhesive including a hot-melt high polymer in 10 to 30 parts by weight, alicyclic petroleum resin in 10 to 50 parts by weight, and softener in 10 to 45 parts by weight.

The compress is not limited as long as it produces a hot compress effect regardless of presence of moisture. Specifically, a known compress may be used.

In the present invention, the adhesive layer may be formed over one entire surface of the pouch, or in stripes, in lattice shape, in sports or partially thereon.

The adhesive layer need not be crosslinked. However, the adhesive layer should preferably be crosslinked from the viewpoint of enhancing thermal stability, maintenance of adhesive strength when heated, maintenance of shape when heated, avoidance of loosening and stickiness when heated, diminishment of remaining paste upon separation to improve comfort of use, and improved support for medication.

The adhesive layer may be crosslinked through chemical crosslinking using a chemical crosslinking agent. The adhesive layer may be physically crosslinked by ultraviolet radiation or electron beam radiation.

The physical crosslinking with ultraviolet or electron beam radiation may be carried out after the adhesive layer is formed on the pouch. Alternatively, the adhesive layer may be formed in a predetermined shape on a carrier, crosslinked and placed on the pouch such as by transfer.

The physical crosslinking may be carried out following a method as described in Japanese Patent Publication No. 62-39184, for example. Normally, ultraviolet radiation may be performed with a wavelength of 200 to 680 nm for 5 to 30 minutes. Electron beam radiation may be performed in 1 to 20 Mrad for 0.01 to 5 seconds.

The adhesive layer used in the present invention is not limited to a particular thickness as long as it exhibits an adhesive strength to hold the application pad according to the present invention to a location of application. Generally, a preferred thickness in the range of 5 to 3000 $\mu$m, particularly the range of 10 to 1000 $\mu$m. A thickness below 5 $\mu$m may not provide a required adhesive strength. A thickness exceeding 3000 $\mu$m is not only meaningless but is too thick to give a comfortable feeling in use.

Preferably the application pad according to the present invention includes skin absorbable medication carried by the adhesive layer or between the pouch and adhesive layer, to produce a general or local therapeutic effect.

The application pad according to the present invention may be used in a therapeutic system for continuously supplying medication to a living body through the skin to expect a general or local therapeutic effect. In this case, skin absorbable medication may be carried by the pouch as blended into the adhesive layer. Alternatively, skin absorbable medication may be included in the form of a medication storing layer provided between the pouch and adhesive layer.

Where a medication storing layer is provided between the pouch and adhesive layer, release of medicinal ingredients is controlled by means of a release control film or by scattering within the medication storing layer. Where the adhesive layer includes skin absorbable medication, release of medicinal ingredients is controlled by scattering within the adhesive layer.

The skin absorbable medication is not limited as long as it is skin absorbable. Specific examples thereof include a skin stimulant, anodyne/antiphlogistic, central nerve active agents (soporific/sedative, psychoneurotic agent, etc.), diuretic, hypotensive, coronary vasodilator, antihistaminic, anti-arrhythmic, cardiac, adrenocortical hormone drug, and local anesthetic. One type of these medicines, or two or more types thereof, is/are used.

The amount of medication used is not limited as long as a medical effect is expected, but may be determined from the point of view of pharmacological effect and economy, and from the point of view of adhesion where the medication is mixed into the adhesive layer.

Specifically, the skin absorbable medication may be contained in the range of 0.01 to 25 parts by weight, and preferably 0.5 to 15 parts by weight, in relation to 100 parts by weight of the adhesive (solid).

The skin absorbable medication contained in less than 0.01 parts by weight produces little medicinal effect. The medication exceeding 25 parts by weight is not only meaningless but uneconomical.

The application pad according to the present invention may include a far infrared radiator contained in or carried by at least one of the exothermic composition, pouch and adhesive layer, and/or between the pouch and adhesive layer, to promote the heating effect with far infrared radiation.

Specifically, for example, a ceramic material radiating far infrared rays (far infrared radiator) may be enclosed in the pouch, or carried by the pouch by applying a coating containing the far infrared radiator to one surface of the pouch, and drying the coating thereon. The far infrared radiator may be carried between one surface of the pouch and the adhesive layer formed thereon in the form of the ceramic material radiating far infrared rays. The far infrared radiator may be carried by the adhesive layer in the form of the ceramic material radiating far infrared rays mixed into the adhesive layer formed on one surface of the pouch.

The ceramic material radiating far infrared rays may be used together with or in place of the exothermic composition. This ceramic material may be enclosed in the pouch along with the exothermic composition, or may be carried by a carrier as is the exothermic composition. Further, the ceramic material may be carried by the adhesive layer.

In this case, the heating effect promotes blood circulation. When used with the skin absorbable medication, the ceramic material increases the skin absorbability of the medication to enhance the general or local therapeutic effect.

The application pad according to the present invention may include a magnetic substance contained in or carried by at least one of the exothermic composition, pouch and adhesive layer, and/or between the pouch and adhesive layer, to produce a magnetic therapeutic effect with the magnetism of the magnetic substance.

The application pad according to the present invention includes the exothermic device according to the present invention, and an adhesive layer formed on one surface of the pouch of the exothermic device. The application pad may be applied directly to a surface of the human body or the like, or to underwear or a sock. In tight contact with the human body, the application pad provides a heating and stimulating effect while avoiding a displacement during use.

The most important feature of the application pad according to the present invention is that the exothermic temperature of the exothermic device is controlled not to exceed a safety temperature regardless of the gas permeability and moisture permeability of the pouch, variations in the exothermic composition and ambient temperature. Or the time in which the safety temperature is exceeded is limited within a safety period. Consequently, a low-temperature burn is avoided reliably.

Where the application pad includes skin absorbable medication carried by the pouch or adhesive layer or between the pouch and adhesive layer, the skin absorbable medication is prevented from being absorbed in excess due to a high temperature. Particularly where the exothermic composition includes a water retainer comprising a highly absorptive polymer to maintain a lower limit temperature above a predetermined temperature, the skin absorbable medication is prevented from being absorbed insufficiently due to a low temperature.

Where the application pad according to the present invention includes a far infrared radiator carried by at least one of the exothermic composition, pouch and adhesive layer and/or between the pouch and adhesive layer, the infrared radiation promotes the heating effect and blood circulation, thereby enhancing the general or local therapeutic effect. Particularly where skin absorbable medication is used in combination, the skin absorption of the medication is increased.

In addition, where the application pad according to the present invention includes a magnetic substance contained in or carried by the pouch, the magnetism of the magnetic substance produces a magnetic therapeutic effect.

The application pad according to the present invention includes an adhesive layer formed on one surface of the pouch of the exothermic device. The exothermic temperature may be limited to a safety temperature (approximately 43° C.) causing no low-temperature burn, or the time in which the safety temperature is exceeded is limited to a safety period to avoid a low-temperature burn. By virtue of the adhesive strength of the adhesive layer, the application pad may be applied directly to a surface of the human body or the like. The application pad may be used safely during a period of sleep while avoiding a displacement during use. The application pad enhances the heating and stimulating effect through tight contact with a surface of a living body such as a human body.

Where the application pad includes skin absorbable medication carried by the pouch or adhesive layer or between the pouch and adhesive layer, the skin absorbable medication is prevented from being absorbed in excess due to a high temperature. Particularly where the exothermic composition includes a water retainer comprising a highly absorptive polymer to maintain a lower limit temperature above a predetermined temperature, the skin absorbable medication is prevented from being absorbed insufficiently due to a low temperature.

Where the application pad according to the present invention includes a far infrared radiator carried by at least one of the exothermic composition, pouch and adhesive layer and/or between the pouch and adhesive layer, the infrared radiation promotes the heating effect and blood circulation, thereby enhancing the general or local therapeutic effect. Particularly where skin absorbable medication is used in combination, the skin absorption of the medication is increased.

In the application pad according to the present invention, where the far infrared radiator is carried by the pouch, the heating effect enhances a general physical function such as blood circulation. Particularly where skin absorbable medication is used in combination, the skin absorption of the medication is increased to promote the general or local therapeutic effect. Particularly when applied to the human body, and the exothermic device repeats temperature increase and decrease with a range of 37 to 43° C., a type of massaging effect is produced to promote the therapeutic effect still further.

In addition, where the application pad according to the present invention includes a magnetic substance carried by the pouch, the magnetism of the magnetic substance produces a magnetic therapeutic effect.

Other features and advantages of the present invention will be apparent from the following description.

DETAILED DESCRIPTION OF THE PREFERRED EMBODIMENTS

Embodiments of the present invention will particularly be described hereinafter with reference to the drawings. It should be understood, however, that the present invention are not limited to these embodiments.

In a first embodiment of the invention, a mixture A was first obtained by compounding and mixing iron powder in 97 parts by weight, carbon black (MA100 manufactured by Mitsubishi Kagaku K. K.) in 3.5 parts by weight, a water absorber (Metolose SM-4000 manufactured by Shinetsu Kagaku K. K.) in 3 parts by weight, and a water absorber (CS-6HS manufactured by Nihon Shokubai K. K.) in 3 parts by weight.

On the other hand, a mixture B was obtained by compounding and mixing the water absorber (Metolose SM-4000 manufactured by Shinetsu Kagaku K. K.) in 12 parts by weight, carbon powder (MA100 manufactured by Mitsubishi Kagaku K. K) in 75 parts by weight, common salt in 18.75 parts by weight, water in 375 parts by weight, a surface active agent (EP Powder manufactured by Kao Corp.) in 3.75 parts by weight, and sodium tripolyphosphate (pH regulator) in 1.0 part by weight.

Figure 1:
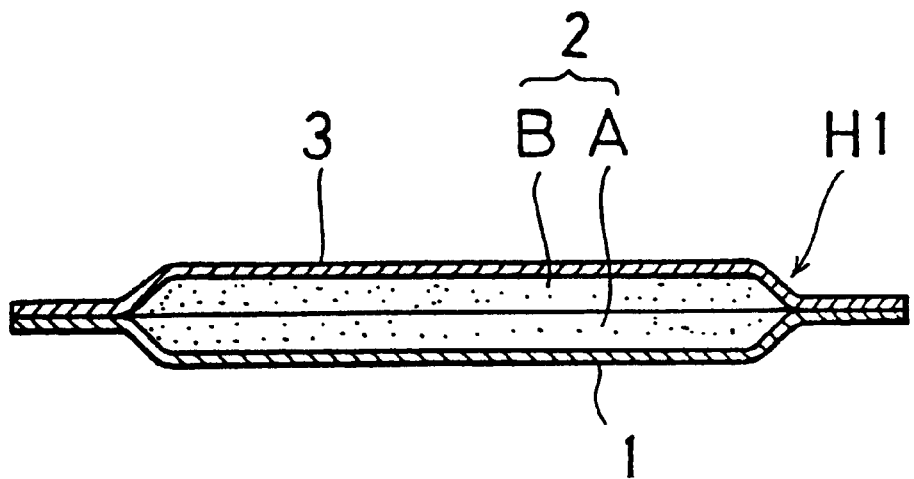
FIG. 1 is a schematic sectional view of an exothermic device in a first embodiment of the present invention.

Next, as shown in FIG. 1, 3.0 g of the above mixture B was transferred onto a second sheet 3, 130×95 mm, formed of a nonwoven fabric of polyester. Immediately thereafter, 4.44 g of the above mixture A was transferred onto the mixture B. Thus, a total of 7.44 g of an exothermic composition was transferred. Immediately after this, a first sheet 1, 130×95 mm, formed of a porous film with a nonwoven fabric of polyamide (water-vapor permeability: 430 g/m² a day) was superposed thereon, and the edges were joined by heat sealing. In this way, an exothermic device H1 according to the present invention was obtained.

Figure 2:
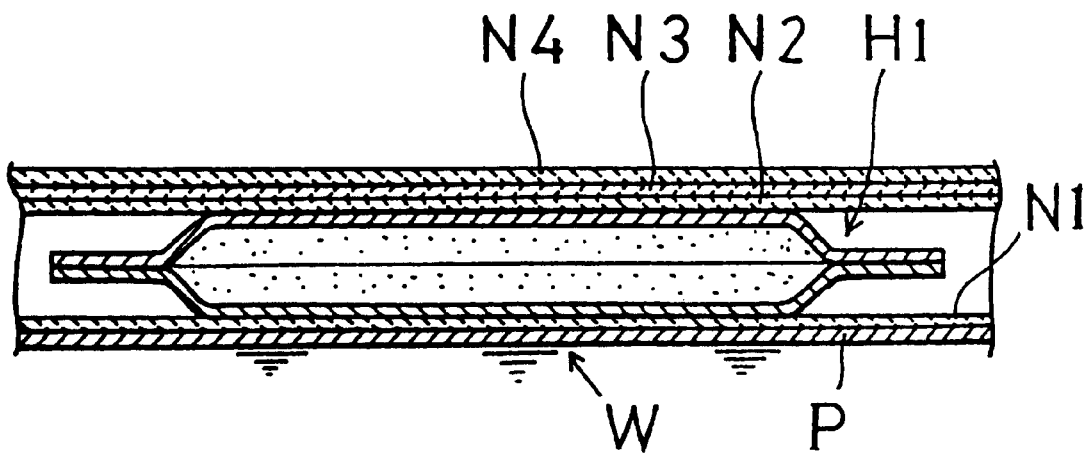
FIG. 2 is a schematic view showing a procedure for measuring a heating temperature of the exothermic device according to the present invention.

Next, as shown in FIG. 2, a stainless steel plate P was placed on warm water W at 35° C. A first flannel sheet N1 was placed on the stainless steel plate P, and then the above exothermic device H1 was placed thereon. Further, three, second to fourth, flannel sheets N2-N4 were placed on the exothermic device H1. A dummy skin temperature was measured between the exothermic device H1 and the first flannel sheet N1, regarding a surface temperature on the first flannel sheet N1 as the dummy skin temperature. The measurement gave temperature variations as shown in line "a" in FIG. 3.

Figure 3:
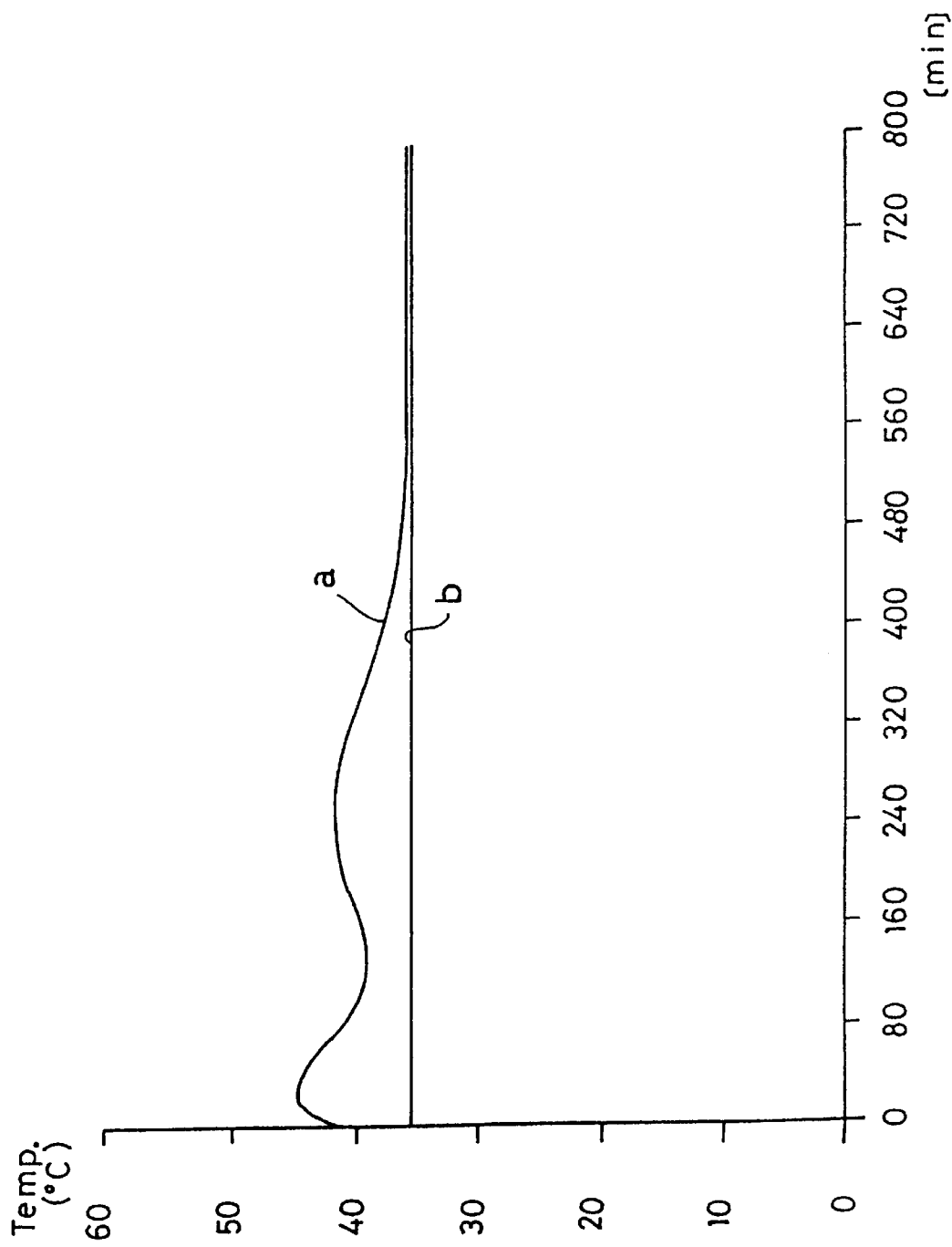
FIG. 3 is a view showing exothermic temperature characteristics of the exothermic device in the first embodiment of the present invention.

As shown in line "a" in FIG. 3, the temperature reached 43° C. about 4 minutes from start of the temperature measurement. Then, about 20 minutes thereafter, the exothermic temperature reached approximately 44° C. Subsequently, the temperature lowered gradually to 43° C. in about 32 minutes, to 40° C. about 45 minutes therefrom, and further down to 39° C. about 36 minutes therefrom. Then, the temperature began to increase to reach 41.7° C., and thereafter lowered again gently. It has been noted that the temperature approaches the dummy skin temperature (line "b") of 35° C. approximately 560 minutes from the start of the temperature measurement.

The exothermic temperature decreases gradually from about 44° C. because the water absorber releases adsorbed water, and the released water is adsorbed by the iron powder to form barrier layers, thereby impairing contact between the iron powder and air to retard the exothermic reaction. It has been observed that the temperature rises again after the decrease. This is understood to be due to the temperature decrease of the exothermic composition 2 whereby the water absorber absorbs free moisture from around the iron powder to eliminate the barrier layers, which in turn reactivates the exothermic reaction of the exothermic composition 2.

The reason for the second temperature increase being slack and the peak of the second temperature increase being lower than that of the first temperature increase is understood to be that part of the iron powder in the exothermic composition 2 has undergone a reaction whereby the iron powder has become less fresh. In addition, it is understood that no temperature increase takes place after the second temperature decrease because a further change has occurred in the balance of water in the exothermic composition 2 after the second temperature increase.

Thus, the exothermic temperature temporarily reaches a temperature which may cause a low-temperature burn, but the exothermic temperature is at a relatively low temperature of 44° C. Where the period in which the temperature exceeds 43° C. is a short period in the order of 30 minutes, a direct contact of the exothermic device H1 with the human skin has no likelihood of causing a low-temperature burn. This provides enhanced safety.

In a second embodiment of the invention, a mixture A was obtained by compounding and mixing iron powder in 97 parts by weight, carbon powder (MA100 manufactured by Mitsubishi Kagaku K. K.) in 1.5 parts by weight, and a water absorber (CS-6HS manufactured by Nihon Shokubai K. K.) in 3 parts by weight.

On the other hand, a mixture B was obtained by compounding and mixing a water absorber (Metolose SM-4000 manufactured by Shinetsu Kagaku K. K.) in 16.6 parts by weight, carbon powder (MA100 manufactured by Mitsubishi Kagaku K. K) in 100 parts by weight, and sodium chloride in 33 parts by weight, and thereafter adding water in 512 parts by weight.

Figure 4:
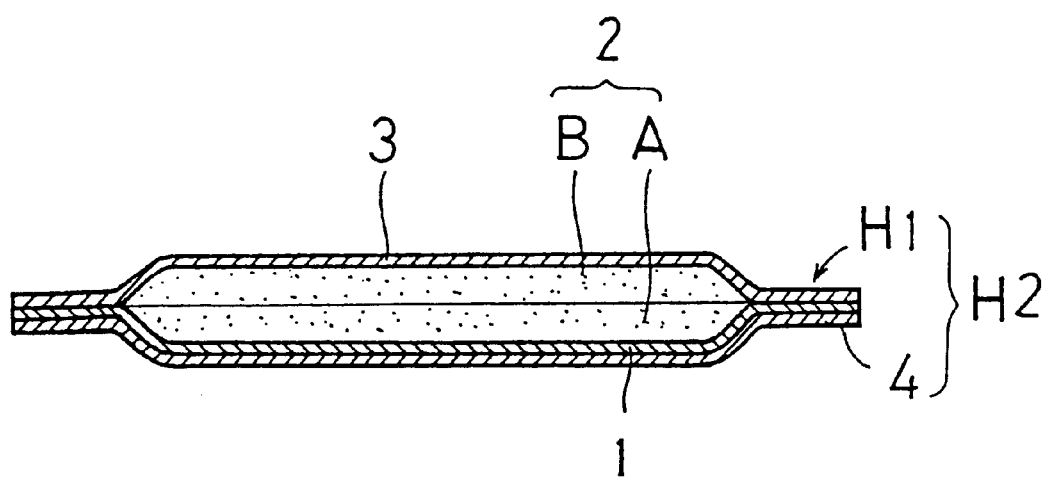
FIG. 4 is a schematic sectional view of an exothermic device in a second embodiment of the present invention.

Next, as shown in FIG. 4, as in the first embodiment, 3.2 g of the above mixture B was transferred onto a second sheet 3, 130×95 mm, formed of a nonwoven fabric of polyester. Immediately thereafter, 6.2 g of the above mixture A was transferred onto the mixture B. Thus, a total of 9.4 g of an exothermic composition 2 was transferred. Immediately after this, a first sheet 1, 130×95 mm, formed of a porous film with a nonwoven fabric of polyamide (water-vapor permeability: 350 g/m² a day) was superposed thereon, and the edges were joined by heat sealing. In this way, an exothermic device H1 according to the present invention was obtained.

Further, an acrylic adhesive was applied to and dried on the polyester nonwoven fabric of the exothermic device H1 to form an adhesive layer 4 having a thickness of 25 μm. In this way, an application pad H2 according to the present invention was obtained.

Next, as shown in FIG. 2, a stainless steel plate P was placed on warm water W at 35° C. A first flannel sheet N1 was placed on the stainless steel plate P, and then the above application pad H2 was applied thereto. Further, three, second to fourth, flannel sheets N2-N4 were placed on the application pad H2. A dummy skin temperature was measured between the exothermic device H1 and the first flannel sheet N1, regarding a surface temperature on the first flannel sheet N1 as the dummy skin temperature. The measurement gave temperature variations as shown in line "c" in FIG. 5.

Figure 5:
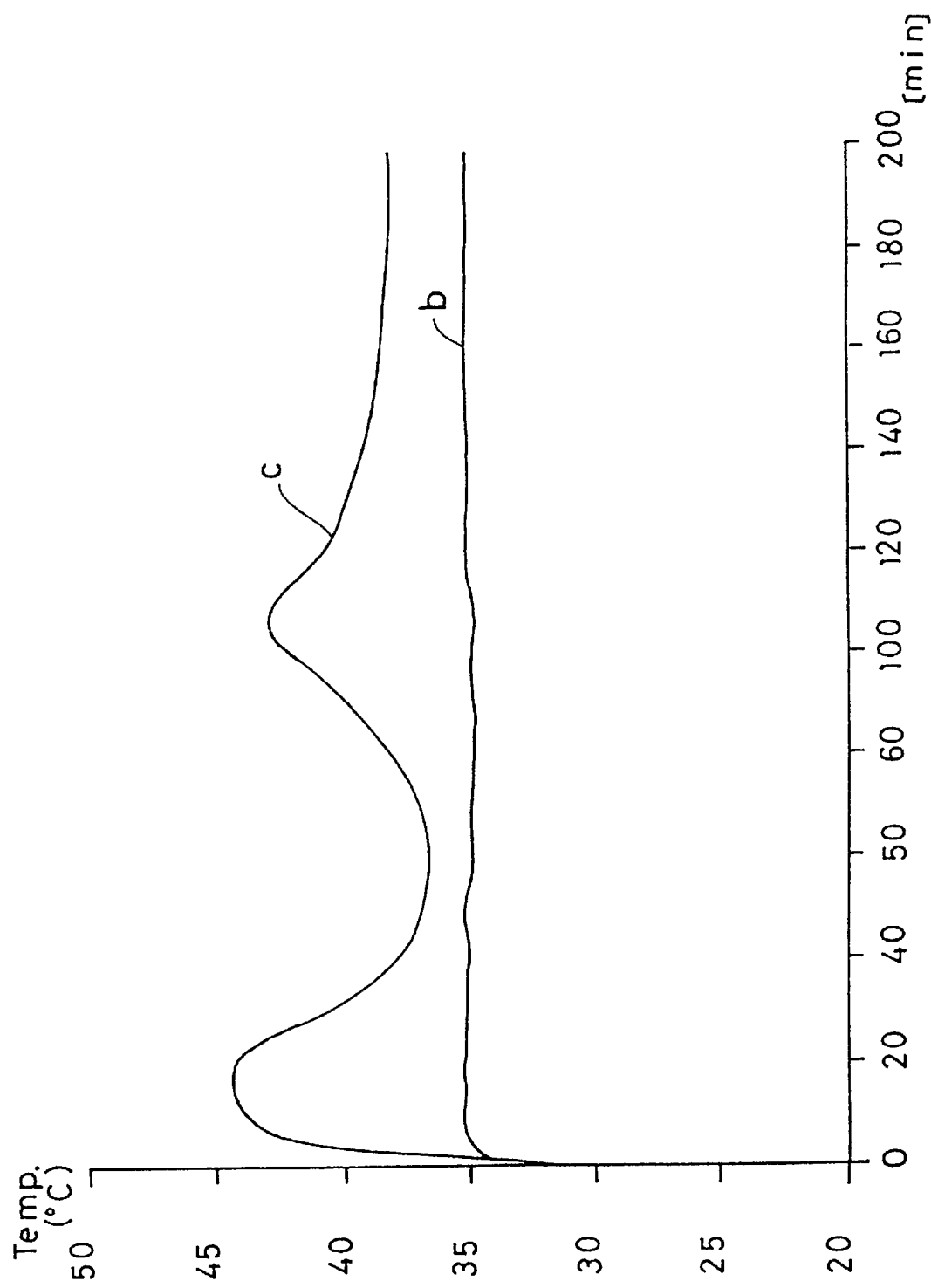
FIG. 5 is a view showing exothermic temperature characteristics of the exothermic device in the second embodiment of the present invention.

As shown in line "c" in FIG. 5, the temperature reached 43° C. about 7 minutes from start of the temperature measurement. Then, about 12 minutes thereafter, the exothermic temperature reached approximately 44° C. Immediately thereafter, the temperature lowered rapidly to 43° C. in about 6 minutes, and to 40° C. about 7 minutes therefrom. The temperature once lowered to 36.5° C. about 51 minutes from the start of the temperature measurement, and then gradually increased to reach 42.7° C. about 110 minutes therefrom. Further, the temperature gradually decreased and remained at 40 to 38° C. for 460 minutes. It has been noted that the temperature approaches the dummy skin temperature (line "b") of 35° C. approximately 620 minutes from the start of the temperature measurement.

In the second embodiment, when the exothermic temperature exceeds 43° C., the water absorber releases adsorbed water, and the released water is adsorbed by the iron powder to form barrier layers, thereby impairing contact between the iron powder and air to retard the exothermic reaction and lower the exothermic temperature. When the exothermic temperature becomes 36.5° C., the water absorber absorbs free moisture from around the iron powder to eliminate the barrier layers, which reactivates the exothermic reaction of the exothermic composition 2. The second peak temperature reaches a level close to the first peak temperature. A heat of about 38° C. is obtained approximately 180 minutes from the start of the temperature measurement.

The temperature reached about 38° C. after lapse of about 180 minutes though the first temperature decrease was to about 36.5° C. This is understood due to a gradual increase in adsorption per unit time by the water absorber occurring during the slack temperature increase. It is understood that the temperature increase takes place twice only because of a diminishment of the iron powder taking part in the exothermic reaction, a less quantity of water being released during the first temperature increase, a less quantity of adsorbed water being released by the water absorber during the second temperature increase, and a still less quantity of adsorbed water being released by the water absorber during the second temperature decrease.

The application pad H2 in this embodiment exceeds a safety temperature for about 10 minutes only. There is no possibility of low-temperature burn and therefore it is safe even if the application pad H2 is maintained in direct contact with the human skin for a long time.

In a third embodiment of the invention, a mixture A was first obtained by compounding and mixing iron powder in 97 parts by weight, and a water absorber (CS-6HS manufactured by Nihon Shokubai K. K.) in 3 parts by weight.

On the other hand, a mixture B was obtained by compounding and mixing a water absorber (Metolose SM-4000 manufactured by Shinetsu Kagaku K. K.) in 20.8 parts by weight, activated carbon (Takeda-C manufactured by Takeda Yakuhin K. K.) in 150 parts by weight, sodium chloride in 41.2 parts by weight, and water in 515.2 parts by weight.

Figure 6:
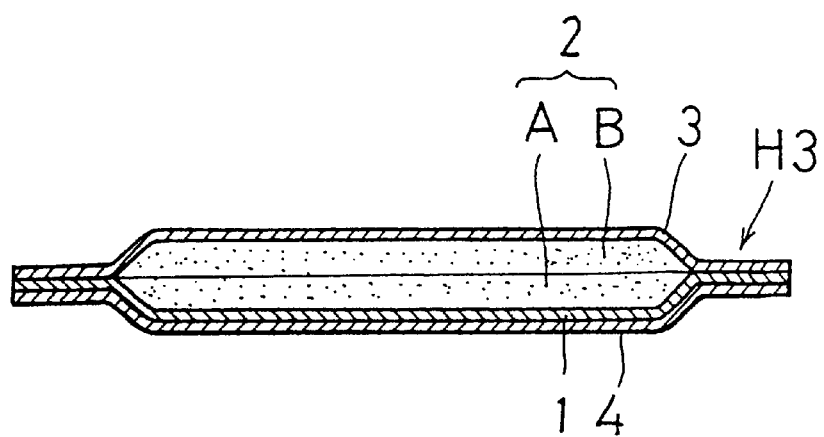
FIG. 6 is a schematic sectional view of an exothermic device in a third embodiment of the present invention.

Next, as shown in FIG. 6, as in the first embodiment, 5.1 g of the above mixture A was transferred onto a first sheet 1, 130×95 mm, formed of a porous polyethylene film (water-vapor permeability: 350 g/m² a day). Immediately thereafter, 2.45 g of the above mixture B was transferred onto the mixture A. Thus, a total of 7.55 g of an exothermic composition 2 was transferred. Immediately after this, a second sheet 3, 130×95 mm, formed of a porous polyethylene film (water-vapor permeability: 350 g/m² a day) was superposed thereon, and the edges were joined by heat sealing. In this way, an exothermic device according to the present invention was obtained.

Further, an acrylic adhesive was applied to and dried on one surface of the exothermic device to form an adhesive layer 4 having a thickness of 25 µm. In this way, an application pad H3 according to the present invention was obtained.

Figure 7:
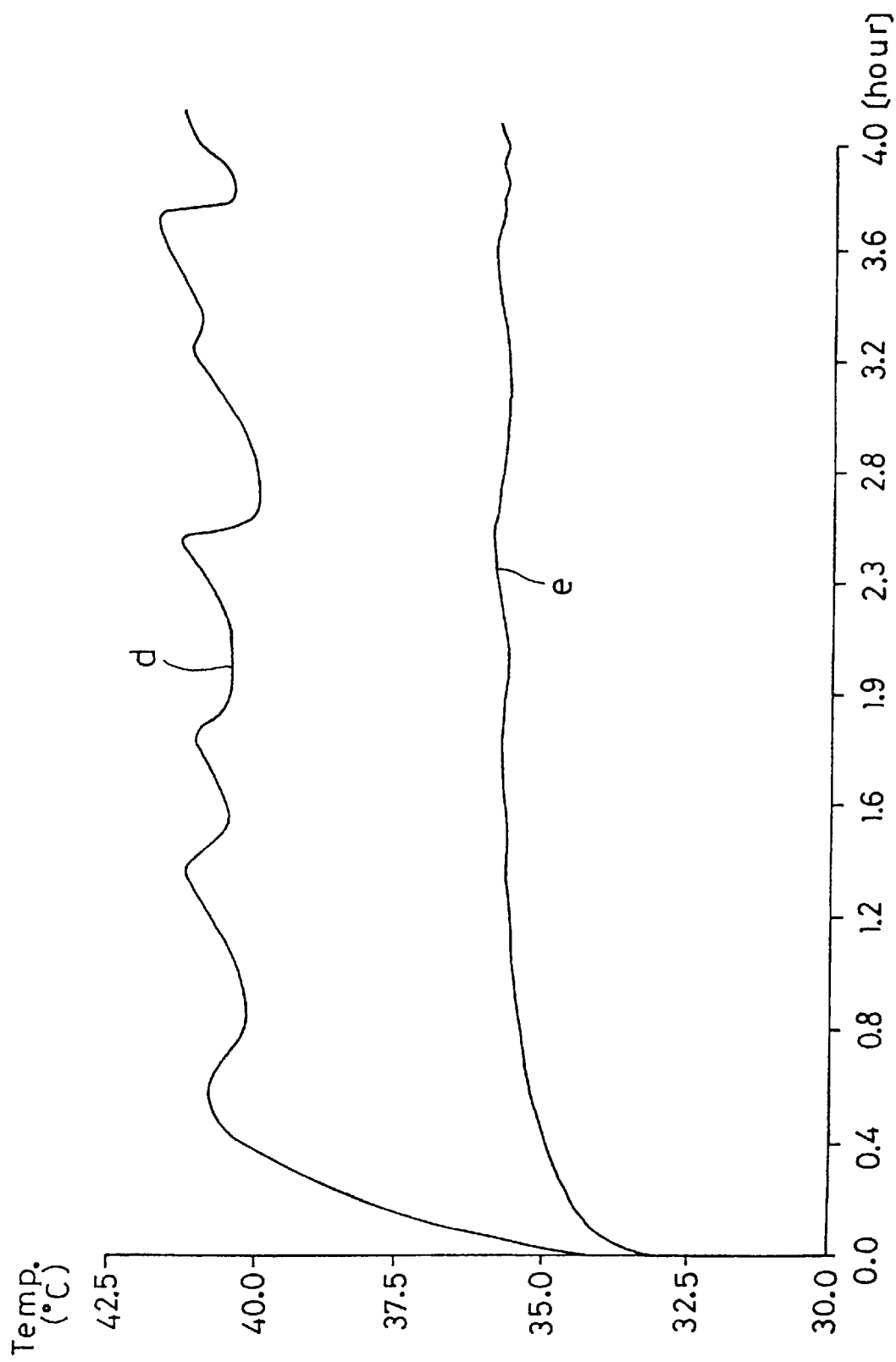
FIG. 7 is a view showing exothermic temperature characteristics of the exothermic device in the third embodiment of the present invention.

The application pad H3 was applied to a human body surface, and temperature variations were measured. As shown in line "d" in FIG. 7, the exothermic temperature reached 40° C. about 22 to 23 minutes from start of the temperature measurement, and rose to 40.8° C. about 12 minutes therefrom. Immediately thereafter, the temperature lowered gradually to 40° C. in about 12 minutes. That is, the exothermic temperature lowered to 40° C. about 47 minutes from the start of the measurement. Further, the temperature gradually increased to reach approximately 41.2° C. about 37 minutes therefrom, i.e. 84 minutes from the start of the temperature measurement. The temperature gradually lowered to 40.4° C. 12 minutes therefrom. Subsequently, as shown in FIG. 7, the temperature repeatedly increased and decreased. These temperature increases and decreases provide a type of massaging effect and control of an absorption rate of skin absorbable medication. Besides, no low-temperature burn was detected.

Line "e" in FIG. 8 represents the skin temperature of a panelist to whom the application pad was not applied.

The foregoing relates to preferred exemplary embodiments of the invention, it being understood that other variants and embodiments thereof are possible within the spirit and scope of the invention, the latter being defined by the appended claims.

What is claimed is:

1. A method of controlling an exothermic reaction of an exothermic device, comprising forming an exothermic composition, during forming said exothermic composition comprising, as essential components thereof, a metal powder, a metallic chloride, and water mixing a water absorber having a water absorptive ability reversibly variable with temperature variations into said exothermic composition, enclosing said exothermic composition and water absorber mixture in a container in which at least a part of said container is gas-permeable, whereby heat is formed when said mixture is in contact with air and said water absorber releases adsorbed water above a predetermined temperature, to increase free moisture, thereby retarding the exothermic reaction.

2. A method of controlling an exothermic reaction of an exothermic device as defined in claim 1, wherein following a decrease in exothermic temperature due to the retardation of the exothermic reaction based on a release of the absorbed water from said water absorber, the exothermic reaction resumes due to the absorption of water by said water absorber.

3. A method of controlling an exothermic reaction of an exothermic device as defined in claim 1, wherein said water absorber comprises a water-soluble cellulose ether.

4. A method of controlling an exothermic reaction of an exothermic device as defined in claim 1, further comprising mixing a water retainer comprising a water absorptive polymer for holding water into the exothermic composition, the water absorbed by said water retainer being gradually released.

5. An exothermic device comprising, as essential components thereof, a metal powder, a metallic chloride, water, and a water absorber having a water absorptive ability reversibly variable with temperature variations due to an exothermic reaction.

6. An exothermic device as defined in claim 5, further comprising a catalyst and/or a pH regulator.

7. An exothermic device as defined in claim 5, further comprising a water retainer.

8. An exothermic device as defined in claim 7, wherein said water retainer is a water-absorptive polymer other than a water-soluble cellulose ether.

9. An exothermic device as defined in claim 5, further comprising an exothermic reaction auxiliary for promoting the exothermic reaction.

10. An exothermic device as defined in claim 5, wherein said water absorber having a water absorptive ability reversibly variable with temperature variations due to the exothermic reaction is a water-soluble cellulose ether.

11. An exothermic device as defined in claim 5, in which said device is enclosed in a flat pouch having at least one gas-permeable surface.

12. An exothermic device as defined in claim 11, wherein said device contains a far infrared radiator.

13. An application pad comprising an exothermic device including as essential components thereof, a metal powder, a metallic chloride, water, and a water absorber having a water absorptive ability reversibly variable with temperature variations due to an exothermic reaction, said exothermic device being enclosed in a flat pouch having at least one gas-permeable surface, and further including an adhesive layer formed on one surface of the flat pouch.

14. An application pad as defined in claim 13, in which said flat pouch further comprises skin absorbable medication mixed in said adhesive layer.

15. An application pad as defined in claim 13, further comprising a far infrared radiator contained or carried in at least one of said exothermic composition, said pouch and said adhesive layer and/or between said pouch and said adhesive layer.

16. An application pad as defined in claim 13, further comprising a magnetic element contained or carried in at least one of said exothermic composition, said pouch and said adhesive layer and/or between said pouch and said adhesive layer.

17. An application pad as defined in claim 13, in which said pouch further comprises skin absorbable medication provided between said pouch and said adhesive layer.

* * * * *